United States Patent
Fishman

[11] Patent Number: 5,824,323
[45] Date of Patent: Oct. 20, 1998

[54] SKIN LOTION COMPOSITION AND SOFTGEL FILLED THEREWITH AND METHODS FOR MAKING AND USING SAME

[75] Inventor: Yoram Fishman, Los Angeles, Calif.

[73] Assignee: Absolute Beauty Company, High Point, N.C.

[21] Appl. No.: 742,365

[22] Filed: Nov. 1, 1996

[51] Int. Cl.⁶ ..................................................... A61K 7/43
[52] U.S. Cl. ............................. 424/401; 424/59; 424/60; 424/63; 206/528; 206/530; 206/531
[58] Field of Search ............................... 424/401, 59, 60, 424/63; 206/528, 530, 531

[56] References Cited

U.S. PATENT DOCUMENTS

| | | | |
|---|---|---|---|
| 4,707,354 | 11/1987 | Garlen et al. | 424/47 |
| 4,760,095 | 7/1988 | Djerassi et al. | 514/847 |
| 4,784,849 | 11/1988 | Tutsky | 424/73 |
| 5,073,372 | 12/1991 | Turner et al. | 424/401 |
| 5,219,558 | 6/1993 | Woodin, Jr. et al. | 424/59 |
| 5,256,404 | 10/1993 | Martino et al. | 424/59 |
| 5,270,054 | 12/1993 | Bertolini | 424/451 |
| 5,310,556 | 5/1994 | Ziegler | 424/401 |
| 5,494,657 | 2/1996 | Swenson et al. | 424/59 |
| 5,496,861 | 3/1996 | Rouse, 3 et al. | 514/778 |

Primary Examiner—Thurman K. Page
Assistant Examiner—D. Faulkner
Attorney, Agent, or Firm—Jeffer, Mangels, Buter & Marmaro LLP

[57] ABSTRACT

There is provided a skin lotion composition with non-greasy skin feel, capable of being stably encapsulated within a softgel, and which may preferably include tocopheryl acetate and/or vitamin A palmitate and methods for making and using the same.

15 Claims, No Drawings

SKIN LOTION COMPOSITION AND SOFTGEL FILLED THEREWITH AND METHODS FOR MAKING AND USING SAME

FIELD OF THE INVENTION

The present invention relates to a skin lotion composition suitable for use in a softgel, preferably a composition containing tocopherol acetate and vitamin A palmitate and methods for making and using the same.

BACKGROUND OF THE INVENTION

A soft, supple and flexible skin has a marked cosmetic appeal and is an attribute of normal functioning epidermis. As human skin ages with advancing years, the epidermis can become folded, ridged or furrowed to form wrinkles. These signal loss of youthful appearance and herald the transition to old age. Exposure to excessive doses of sunlight accelerates the transition process. The outer layer of the epidermis (the stratum corneum) can also become dry and flaky following exposure to cold weather or excessive contact with detergents or solvents. Loss of skin moisture thereby results, and the skin begins to lose the soft, supple and flexible characteristics.

The known skin lotion compositions which may include tocopheryl acetate and/or vitamin A palmitate have typically been prepared in the form of lotions, sprays, creams, molded sticks, and the like, and have been packaged and dispensed from conventional tubes, lidded jars, aerosol or pump spray containers, stick applicators, etc.

Exemplary skin lotion formulations are disclosed by Garlen, U.S. Pat. No. 4,707,354; Djessari, U.S. Pat. No. 4,760,095; Swenson, U.S. Pat. No. 5,494,657; Tutsky, U.S. Pat. No. 4,784,849; and Dixon et al., U.S. Pat. No. 4,701,322. Sunscreen compositions are disclosed by Martino, U.S. Pat. No. 5,256,404; Woodin, U.S. Pat. No. 5,219,558. Ziegler, U.S. Pat. No. 5,310,556 discloses a cosmetic composition.

With the development of the soft gelatin capsule, or softgel, an alternative form of dispensing and applying a skin lotion composition has become available. Encapsulation of a skin lotion composition, preferably vitamin enriched, in a softgel offers numerous advantages. For example, the compositions could be prepared in pre-measured quantities effective to moisturize and vitamin enrich the skin of a user, thus minimizing waste of the compositions.

For practicable encapsulation within a softgel, however, the skin lotion composition must be compatible with the softgel. In particular, the composition must be formulated such that it can be stably encapsulated in the softgel without dissolving the softgel. Preferably, the composition should be formulated such that it is stable in encapsulated form for extended periods of time at room temperature.

A need exists for skin lotion compositions, preferably including tocopheryl acetate and vitamin A palmitate that are compatible with a softgel and can be encapsulated stably in a softgel. Desirably, the compositions should be gentle to the skin as well and have a non-greasy feel when applied to the skin.

SUMMARY OF THE PREFERRED EMBODIMENTS

In accordance with one aspect of the present invention, there is provided a skin lotion composition which has a non-greasy feel when applied to the skin. Rather, the skin lotion has the dry, powdery feel of a water-based lotion and is capable of being stably encapsulated within a softgel.

In accordance with another aspect of the present invention, there is provided a skin lotion composition including at least one vitamin, preferably important to the condition of the skin that is capable of being stably encapsulated within a softgel. Most preferably, the inventive composition includes tocopheryl acetate and vitamin A palmitate.

In accordance with yet another aspect of the present invention there is provided a skin lotion composition which is capable of being stably encapsulated within a softgel which includes, a fine particulate, at least one aliphatic hydrocarbon, a moisturizing agent, and an emulsifying agent.

According to another aspect of the present invention there is provided a skin lotion product comprising a skin lotion composition as described above, encapsulated in a softgel.

According to yet another aspect of the present invention there is provided a skin lotion composition which is capable of being stably encapsulated within a softgel produced by a method which includes the steps of combining: a) a fine particulate; b) an aliphatic hydrocarbon; c) a moisturizing agent; and d) an emulsifying agent.

According to a further aspect of the present invention, there is provided a method for vitamin enriching and conditioning human skin including the steps of dispensing a vitamin-enriched skin lotion composition encapsulated in a vitamin-enriched skin lotion product as described above from its softgel, and applying the composition to the skin.

Other objects, features and advantages of the present invention will become apparent to those skilled in the art from the following detailed description. It is to be understood, however, that the detailed description and specific example, while indicating preferred embodiments of the present invention, are given by way of illustration and not limitation. Many changes and modifications within the scope of the present invention can be made without departing from the spirit thereof, and the invention includes all such modifications.

DETAILED DESCRIPTION OF THE PREFERRED EMBODIMENTS

Applicant has developed skin lotion compositions having a non-greasy feel when applied to the skin which are compatible with encapsulation within a softgel. The skin lotion compositions preferably include at least a vitamin. Preferably, the vitamin is beneficial to the skin. Most preferably the skin lotion contains tocopheryl acetate (vitamin E) and vitamin A palmitate present in an amount effective to provide vitamin enrichment to human skin.

More particularly, the skin lotion compositions according to the invention preferably have a very low equilibrium relative humidity (ERH). The ERH is a measure of the amount of water in a composition that is free, or "active." In most compositions containing water, at least a portion of the water molecules is strongly bound to various sites, in particular polar sites, on the various chemical constituents of the composition. Such sites include hydroxyl groups, carboxyl groups, carbonyl groups, amino groups, and other sites that are capable of binding water by hydrogen bonding, ionic bonding, etc. Additional quantities of water molecules can be bound less strongly, yet still be effectively unavailable as a solvent for the composition or for materials with which the composition comes into contact. The remaining water is unbound, that is, free.

The ERH of a composition is measured by determining the humidity, in an enclosed volume, at which the vapor pressure of water contained in the composition is equal to the vapor pressure of water in the volume of air above the composition. ERH, and the related quantity of water activity (obtained by dividing the measured ERH by 100), can readily be measured using instruments available commercially from, e.g., Rotronic Instrument Corp. (Huntington, N.Y.). Various methods for measuring ERH and water activity are described in R. Marsili, "Water Activity: Why It's Important and How to Measure It," *Food Product Design*, December 1993, pp. 36–41, which is incorporated herein by reference.

Compositions having an ERH of less than about 45%, more preferably between about 0% and about 45%, and most preferably between about 0% and about 20%, have proven suitable for encapsulation according to the invention and are therefore preferred.

Furthermore, the low ERH of the inventive compositions reduces the risk of bacterial contamination. The amount of free water in the inventive compositions in general is too low to support bacterial growth.

The skin lotion of the present invention preferably has a non-greasy feel when applied to the skin. A non-greasy feel is accomplished when a user applying the lotion to the skin would find it comparable in sensation to a lotion which had a water or alcohol base and was not an oil-based or silicone-based lotion. Oil and silicone, while compatible with a softgel, impart a greasy feel to the lotion. However, the use of water, as discussed above, or alcohols in softgels is incompatible with the stability of a softgel. In order to develop a lotion which has a non-greasy feel without using a water or alcohol base, a softgel compatible substance which provides a skin feel similar to a water based lotion was required. The present compositions were therefore developed.

A base for the skin lotion composition which imparts a non-greasy feel to the skin lotion composition may comprise an aliphatic hydrocarbon or a mixture of aliphatic hydrocarbons. It also preferably includes a fine particulate material. Examples of aliphatic hydrocarbons suitable to form the non-greasy base, include isotridecane, isotetradecane, isopentadecane, other aliphatic straight and branched chain hydrocarbons, which may be saturated or unsaturated and mixtures thereof. Additionally, cyclic hydrocarbons, such as cyclopropane through cyclononane and terpenoids, and mixtures thereof may be used. Fine particulate materials including starches, gums and other fine particulate materials similarly compatible with a softgel and providing a non-greasy feel when applied to the skin, and mixtures thereof, are also suitable in the present invention. Examples of suitable starches include, corn, rice, wheat, tapioca, and flours. Gums can include, for example, xanthin, gum arabic and the like and mixtures thereof. The fine particulate materials preferably do not dissolve, but rather form a colloidal suspension, whereby they provide body and thickness to the skin lotion composition. Preferably, the materials have a mesh size of about 325 or less.

Skin lotion compositions which have a skin feel similar to that of a composition containing a base of about 39.5% isododecane or a mixture of isododecane and isohexadecane comprising about 39.5% of the composition of the present invention and which preferably include a fine particulate material, for example, tapioca starch, have a non-greasy feel when applied to the skin, and are compatible with a softgel. Skin lotion compositions formulated from, for example, those compounds listed above, can be tested on humans as would known in the art, to determine through such tests which compositions did not impart a greasy feel to the skin.

The inventive compositions preferably are emulsions.

Emulsions prepared according to the present invention also include an emulsifying agent which is compatible with gelatin and which has a low hydrophilic/lipophilic balance (HLB). The HLB is a numeric rating system for the combined hydrophilic and lipophilic characteristics of an amphiphilic molecule that contains both hydrophilic and lipophilic moieties, and thus is a measure of the emulsifying efficiency of a surfactant. The HLB is related to the polarity of the molecule, the least hydrophilic surfactants having low HLB numbers, and increasing numbers corresponding to increasing hydrophilic character. For example, a non-ionic surfactant having a low HLB value (i.e., less than about 10) is considered soluble in hydrophobic substances and favors water-in-hydrophobic substance emulsions, while a surfactant having a high HLB value (i.e., greater than about 13) is associated with a water-soluble surfactant and favors hydrophobic substance-in-water emulsions.

The assignment of numerical values for HLB based upon chemical groupings in a molecule is given by A. W. Adamson in "Physical Chemistry of Surfactants," 2nd ed. (Interscience Publishers, New York 1967), pp. 520–522. Adamson also provides references to experimental methods for the determination of HLB numbers of amphiphilic molecules. A detailed definition of HLB is also provided by M. J. Schnick, Surfactants Science Series, Vol. 1, Nonionic Surfactants, Chapter 18 (M. Dekker Inc., New York 1967).

For use in the present invention, preferred emulsifying agents are those non-ionic surfactants that are compatible with the gelatin, and has an HLB from about 1 to about 10 wt %. Suitable emulsifying agents include long-chain (preferably $C_{16}$ or higher, e.g., $C_{17-24}$) fatty acid monoesters of polyhydric alcohols, e.g., glyceryl monostearate, glyceryl monopalmitate, glyceryl monoarachidate, glyceryl monobehenate, sorbitan monolaurate, sorbitan monostearate, sorbitan monooleate, and sorbitan trioleate.

Glyceryl monoesters of long-chain fatty acids are particularly preferred. Such emulsifying agents are solid at room temperature. When heated and combined with the other ingredients of the inventive composition, then cooled, these emulsifying agents afford a homogeneous composition in which the internal phase is microencapsulated by the emulsifying agent. Glyceryl monostearate is particularly preferred. Glyceryl palmitate is also highly useful.

Other emulsifying agents which remain liquid at room temperature are also useful. Mixtures of emulsifying agents can also be used if desired.

The emulsifying agent or mixture of agents preferably is present in an amount from about 1 to about 15 wt %. Care should be exercised in selecting the amount of the emulsifying agent or agents, as excessive amounts can promote the formation of micelles and thus can adversely affect the delivery of vitamins to the skin.

The skin lotion composition of the present invention also preferably include moisturizing agents. Examples of suitable moisturizing agents include petrolatum from about 10 to about 30 wt %, rose hips oil, from about 0.01 to about 5.0 wt %, borage oil from about 0.01 to about 5 wt %, jojoba oil, from about 0.01 to about 5.0 wt % and similar compounds, and mixtures thereof. The moisturizing agents when used in conjunction with the non-greasy base provide a skin lotion which provides skin moisturization without a greasy feel when applied to the skin.

Additionally, one or more vitamins may be added to the skin conditioning lotion. Preferably a vitamin or vitamins which are important for healthy skin may be added to the composition. Most preferably vitamin A palmitate, from about 0.01 to about 1.0 wt % and tocopheryl acetate from about 0.01 to about 5.0 wt % are added to the skin lotion composition.

Optionally, skin conditioning compositions according to the invention can include one or more additional cosmetically useful ingredients, preferably those that are hydrophobic and compatible with gelatin. Such ingredients include, for example, fragrances, humectants, sunscreen agents, antiseptics, preservatives, etc. Examples of the foregoing additional ingredients are disclosed in U.S. Pat. No. 4,424,234, to Alderson et al., which is incorporated herein by reference. Moisturizing agents can be employed in amounts up to about 30.0 wt %. Suitable moisturizing agents include, for example, petrolatum, rose hips oil, borage oil and jojoba oil. Other additives can be present in amounts up to about 20 wt %. Such added ingredients preferably include few or no free aldehyde groups, which can adversely affect gelatin by cross-linking it.

The inventive skin conditioning compositions can be packaged, if desired, in conventional packaging such as plastic bottles, tubes, etc. A user can thus dispense the inventive composition from a conventional bottle or tube and apply the composition to his or her skin.

The inventive compositions are particularly suitable for encapsulation in a soft gelatin shell, or softgel (a one-piece, hermetically sealed soft gelatin shell containing a liquid, a suspension, or a semi-solid). Thus, according to a preferred embodiment, a user can dispense the inventive composition from such an encapsulating softgel and apply the composition as described above to his or her skin.

Softgels including the inventive skin conditioning compositions can be produced using any conventional manufacturing process. The most common modern manufacturing process involved in the preparation of softgels is a continuous method whereby two gelatin ribbons pass between twin rotating dies. As the ribbons meet, the liquid to be encapsulated is precisely injected between them. The capsule halves are sealed and ejected by the continuous rotation of the dies. See P. Tyle, Specialized Drug Delivery Systems, Marcel Dekker, Inc. (1990) for a general discussion of softgel manufacturing and production technology, in particular, Chapter 10 by Paul K. Wilkinson and Foo Song Hom.

Various gelatin shell masses can be prepared, depending on the fill properties, climatic conditions, and end use. Typically gelatin formulations include the same basic ingredients, namely, gelatin, a plasticizer such as glycerin, water, and optionally preservatives. The formulations of gelatins are well known to those of ordinary skill in the art.

The typical rotary die process, which requires a flowable liquid or fill, is readily adaptable to accommodate the skin conditioning compositions of the instant invention.

Shell formulations are discussed in Van Hostetler and J. Q. Bellard noted below as well as in "Advances in Softgel Formulation Technology", M. S. Patel, F. S. S. Morton and H. Seager, *Manufacturing Chemists,* July 1989; "Soft Elastic Gelatin Capsules: A Unique Dosage Form", William R. Ebert, *Pharmaceutical Technology,* October 1977; "Soft gelatin capsules: a solution to many tableting problems", H. Seager, *Pharmaceutical Technology,* September 1985; U.S. Pat. No. 4,067,960 to Fadda; U.S. Pat. No. 4,198,391 to Grainger; U.S. Pat. No. 4,744,988 to Brox; and U.S. Pat. No. 4,780,316 to Brox. These references are incorporated herein in their entireties by reference.

After the rotary die process is used to thereby produce gelatin shells having a skin conditioning composition of the instant invention as fill therein, the resulting capsules are typically washed with an evaporatable solvent. Thereafter, the capsules are typically tumble dried in a series of hollow drums with perforated walls. Room air (25° C.) is continuously pumped through the rotating drums. By the time the capsules exit this process, all of the solvent used in washing has typically been evaporated, and a large proportion (50–60%) of the water from the gelatin shell has been removed. Recent developments in drying include bypassing the drum drying stage and having the capsules dried in a drying tunnel or room as discussed below.

After the capsules exit the last drying drum, the capsules are typically spread on drying trays. The final drying phase for softgels is typically accomplished by passing the drying trays through drying tunnels or into drying rooms. Stacks of trays are inserted into drying tunnels or drying rooms, in which controlled temperature air (21°–24° C.) and low relative humidity (20–30%) is continuously circulated. Although additional water can be removed from dry capsules by further heating, for example at 40° C., such a procedure has not been found to be practical or necessary. See Van Hostetler and J. Q. Bellard in *The Theory and Practice of Industrial Pharmacy,* "Capsules", (1970), Chapter 13 at pages 346–383, and in particular at page 380.

The drying time, for most softgels, is 16–24 hours, but can be slightly longer if the softgels are over 20 minims in size or if the softgels contain a non-oily type liquid base. The Karl Fischer test is used for determining water content. The drying occurs typically at about 21° to about 24° C. and at a relative humidity of about 20 to about 40%.

Softgels permitted to come to water equilibrium in this controlled environment are considered "dry". After drying, the capsules are typically inspected and finished using varied known techniques.

A typical gelatin shell formulation includes about 47 wt % gelatin, about 15 wt % glycerin (USP), and about 38 wt % water, optionally with additional colorant materials. Other shell formulations can readily be prepared by one of ordinary skill in the art.

Softgels having the inventive skin conditioning compositions as fill are capable of being stored for extended periods of time, typically up to 24–36 months or longer, at room temperature (25° C.).

The invention is further illustrated by reference to the following non-limiting examples.

EXAMPLE 1

The composition of the present invention may comprise the following:

| INGREDIENT | SOURCE | COMMERCIAL NAME | (WT/WT) PERCENT |
|---|---|---|---|
| TAPIOCA STARCH | NATIONAL STARCH | TAPIOCA STARCH | 5.0–25.0 |
| ISODODECANE | PRESPERSE | PERMETHYL 99A | 0.1–45.0 |
| ISOHEXADECANE | PRESPERSE | PERMETHYL 101A | 0.1–25.0 |
| PETROLATUM | ANY SOURCE | PETROLATUM | 10.0–30.0 |
| GLYCERYL STEARATE | LIPO CHEMICALS | LIPO GMS-450 | 5.0–15.0 |
| TOCOPHERYL ACETATE | ANY SOURCE | VITAMIN E ACETATE | 0.05–0.50 |
| ROSE HIPS OIL | ANY SOURCE | ROSE HIPS OIL | 0.01–0.10 |
| BORAGE OIL | ANY SOURCE | BORAGE OIL | 0.01–0.10 |
| JOJOBA OIL | ANY SOURCE | JOJOBA OIL | 0.01–0.10 |
| VITAMIN A PALMITATE | ANY SOURCE | RETINYL PALMITATE | 0.01–0.10 |
| | | SUM OF PERCENT ------------------> | 100.0 |

EXAMPLE 2

A preferred embodiment of the present invention is the following:

| INGREDIENT | SOURCE | COMMERCIAL NAME | (WT/WT) PERCENT |
|---|---|---|---|
| TAPIOCA STARCH | NATIONAL STARCH | TAPIOCA STARCH | 20.00 |
| ISODODECANE | PRESPERSE | PERMETHYL 99A | 20.00 |
| ISOHEXADECANE | PRESPERSE | PERMETHYL 101A | 19.45 |
| PETROLATUM | ANY SOURCE | PETROLATUM | 28.00 |
| GLYCERYL STEARATE | LIPO CHEMICALS | LIPO GMS-450 | 12.00 |
| TOCOPHERYL ACETATE | ANY SOURCE | VITAMIN E ACETATE | 0.20 |
| ROSE HIPS OIL | ANY SOURCE | ROSE HIPS OIL | 0.10 |
| BORAGE OIL | ANY SOURCE | BORAGE OIL | 0.10 |
| JOJOBA OIL | ANY SOURCE | JOJOBA OIL | 0.10 |
| VITAMIN A PALMITATE | ANY SOURCE | RETINYL PALMITATE | 0.05 |
| | | SUM OF PERCENT ------------------> | 100.00 |

It is to be understood that the commercial names and sources set forth above are not intended to be limiting and that other commercial designations and/or sources of the same or similar products could be readily determined by those of ordinary skill in the art.

The compositions of the present invention may be formulated as follows: A moisturizer, for example, petrolatum and an emulsifying agent, for example, glyceryl stearate can be combined with stirring over heat until a temperature of 65 to 70) degrees C. is reached. The mixing should continue until the phase is liquid and clear. The heat should be turned off and the base, for example, isohexadecane, moisturizing agents, for example, rose hips oil, borage oil, jojoba oil, and the vitamins, for example, tocopheryl acetate and retinyl palmitate should preferably be added one at a time, with mixing in between addition of each to insure good incorporation. After mixing until uniform, another component of the base, for example, isododecane can be added and mixed until uniformly incorporated. The final element of the base, for example, tapioca starch can be added with rapid stirring at a temperature of about 60 degrees C. Mixing should continue until good incorporation is accomplished at which time the heat is turned off. Stirring can cease when the temperature reaches 55 degrees C. or when the mixture begins to thicken up.

While the description above refers to particular embodiments of the present invention, it will be understood that many modifications can be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A skin lotion composition consisting essentially of:
   a) a fine particulate;
   b) at least one aliphatic hydrocarbon;
   c) a moisturizing agent; and
   d) an emulsifying agent.

2. A skin lotion composition which comprises
   a) tapioca starch from about 5.0 to about 20.0 wt %;
   b) isododecane from about 0.1 to about 45.0 wt %;

c) isohexadecane from about 0.1 to about 25.0 wt %;

d) petrolatum from about 10.0 to about 30.0 wt %;

e) rose hips oil from about 0.01 to about 0.10 wt % f) borage oil from about 0.01 to about 0.10 wt % g) jojoba oil from about 0.01 to about 0.10 wt % h) glyceryl stearate from about 5.0 to about 15.0 wt %.

3. The composition of claim 2 further comprising tocopheryl from about 0.01 to about 0.50 wt % and vitamin A palmitate from about 0.01 to about 0.10 wt %.

4. A skin lotion product comprising the composition of claim 1 encapsulated in a softgel.

5. A skin lotion product comprising the composition of claim 2 encapsulated in a softgel.

6. A skin lotion composition which is capable of being stably encapsulated within a softgel produced by a method comprising the step of combining:

a) a fine particulate comprising tapioca starch, from about 5.0 to about 20.0 wt %, b) at least one aliphatic hydrocarbon selected from the group consisting of isododecane from about 0.1 to about 45.0 wt %, and isohexadecane from about 0.1 to about 25.0 wt %, and combinations thereof, c) a moisturizing agent selected from the group consisting of petrolatum oil from about 10.0 to about 30.0 wt %, rose hips oil from about 0.01 to about 0.10 wt %, borage oil from about 0.01 to about 0.10 wt %, jojoba oil from about 0.01 to about 0.10 wt %, and combinations thereof and, d) an emulsifying agent comprising glyceryl stearate from about 5.0 to about 15.0 wt %.

7. A skin lotion composition which is capable of being stably encapsulated within a softgel produced by a method comprising the steps of:

a) combining petrolatum and glyceryl stearate;

b) stirring the mixture of step a) over heat until a temperature of about 65 to about 70 degrees C. is reached;

c) continuing said stirring until said mixture is liquid and clear d) turning off said heat and combining tocopheryl acetate, isohexadecane, rose hips oil, borage oil, jojoba oil, and retinyl palmitate with the mixture of step c) and mixing until uniform;

e) combining isododecane with the mixture of step d; and f) combining tapioca starch with the mixture of step e), with rapid stirring at a temperature of about 60 degrees C.

8. A skin lotion product comprising the formulation of claim 6 encapsulated in a softgel.

9. A method for conditioning human skin comprising the steps of dispensing the composition encapsulated in the skin lotion product of claim 1 from said softgel and applying said composition to said skin.

10. A method for conditioning human skin comprising the steps of dispensing the composition encapsulated in the skin lotion product of claim 2 from said softgel and applying said composition to said skin.

11. A skin lotion composition consisting essentially of a base which provides a non-greasy feel when applied to the skin, said skin lotion composition capable of being stably encapsulated within a softgel.

12. A skin lotion composition which comprises:

a) fine particulate from about 5.0 to about 20.0 wt %;

b) at least one aliphatic hydrocarbon from about 0.1 to about 45.0 wt %;

c) a moisturizing agent from about 0.1 to about 30.0 wt %;

d) an emulsifying agent from about 5.0 to about 15.0 wt %;

and which excludes silicones.

13. A skin lotion composition consisting essentially of:

a) a fine particulate selected from the group consisting of tapioca starch, corn starch, rice starch, wheat starch, xanthin, and gum arabic and combinations thereof;

b) at least one hydrocarbon selected from the group consisting of saturated or unsaturated aliphatic straight chain hydrocarbons, saturated or unsaturated aliphatic branched chain hydrocarbons, cyclic hydrocarbons, terpenoids, and combinations thereof;

c) a moisturizing agent selected from the group consisting of petrolatum, rose hips oil, borage oil, jojoba oil and combinations thereof; and d) an emulsifier comprising a glyceryl monoester of a long-chain fatty acid.

14. The skin lotion composition of claim 6 further comprising the step combining at least one vitamin with said a)–d).

15. The skin lotion composition of claim 14 wherein said at least one vitamin comprises tocopheryl acetate and vitamin A palmitate.

* * * * *